(12) United States Patent
Carr

(10) Patent No.: US 8,515,554 B2
(45) Date of Patent: *Aug. 20, 2013

(54) RADIOMETRIC HEATING/SENSING PROBE

(75) Inventor: Kenneth L. Carr, Woolwich, ME (US)

(73) Assignee: Meridian Medical Systems, LLC, Portland, ME (US)

( * ) Notice: Subject to any disclaimer, the term of this patent is extended or adjusted under 35 U.S.C. 154(b) by 536 days.

This patent is subject to a terminal disclaimer.

(21) Appl. No.: 12/626,004

(22) Filed: Nov. 25, 2009

(65) Prior Publication Data

US 2010/0076424 A1    Mar. 25, 2010

Related U.S. Application Data

(63) Continuation-in-part of application No. 11/474,883, filed on Jun. 26, 2006, now Pat. No. 7,769,469.

(51) Int. Cl.
  *A61B 18/18*    (2006.01)
(52) U.S. Cl.
  USPC .............................. 607/101; 606/31; 606/33
(58) Field of Classification Search
  USPC ....................................... 607/101; 606/31, 33
  See application file for complete search history.

(56) References Cited

U.S. PATENT DOCUMENTS

| | | | |
|---|---|---|---|
| 3,355,679 A * | 11/1967 | Carr ................................. 333/1.1 |
| 4,557,272 A | 12/1985 | Carr | |
| 4,583,556 A | 4/1986 | Hines et al. | |
| 5,364,336 A | 11/1994 | Carr | |
| 5,531,662 A | 7/1996 | Carr | |
| 5,683,382 A | 11/1997 | Lenihan et al. | |
| 5,688,050 A | 11/1997 | Sterzer et al. | |
| 5,974,343 A | 10/1999 | Brevard et al. | |
| 6,424,869 B1 | 7/2002 | Carr et al. | |
| 6,496,738 B2 | 12/2002 | Carr | |
| 6,932,776 B2 | 8/2005 | Carr | |
| 7,769,469 B2 * | 8/2010 | Carr et al. ...................... 607/101 |
| 7,933,660 B2 * | 4/2011 | Carr ............................. 607/102 |
| 2004/0243004 A1 | 12/2004 | Carr | |
| 2004/0249272 A1 | 12/2004 | Carr | |
| 2004/0267115 A1 * | 12/2004 | Carr ............................. 600/433 |
| 2005/0203388 A1 * | 9/2005 | Carr ............................. 600/430 |
| 2007/0083244 A1 * | 4/2007 | Stevenson et al. .............. 607/37 |
| 2007/0299488 A1 | 12/2007 | Carr | |

FOREIGN PATENT DOCUMENTS

| JP | A 5-253239 | 10/1993 |
|---|---|---|
| JP | A 2005-40307 | 2/2005 |

* cited by examiner

*Primary Examiner* — Roy D. Gibson
*Assistant Examiner* — Kaitlyn Smith
(74) *Attorney, Agent, or Firm* — Cesari and McKenna, LLP

(57) ABSTRACT

A radiometric heating/sensing probe for radiating electromagnetic waves of a first frequency capable of heating tissue and detecting electromagnetic waves of a second frequency emitted by the tissue indicating tissue temperature. The probe includes a dual frequency antenna, a signal transmitting path to the antenna and a signal receiving path from the antenna to a radiometer. A diplexer connected between those paths inside the probe includes a quarter wave stub in the form of a shorted slab line-type transmission line in the signal transmitting path. The entire probe package is only about 0.4 in. long and 0.08 in. in diameter so that it can be used in many minimally invasive applications.

20 Claims, 10 Drawing Sheets

RADIOMETRIC HEATING/SENSING PROBE

RELATED APPLICATION

This application is a continuation-in-part of Ser. No. 11/474,883, filed Jun. 26, 2006; now U.S. Pat. No. 7,769,469.

BACKGROUND OF THE INVENTION

This invention relates to an integrated antenna catheter or probe which relies on electromagnetic radiation to simultaneously controllably heat, and detect the temperature of, fluid or tissue adjacent to the probe. By placing the probe at the region of interest in the body, one can detect, diagnose and treat certain abnormalities associated with tumors, cardiac arrhythmias, benign prosthetic hyperplasia (BPH) and the like. When placed in a patient's vascular system, the catheter or probe can be used to measure temperature or even to raise tissue temperature during heart surgery. It relates especially to an improved probe of the type described in the above application Ser. No. 11/474,883, the entire contents of which are hereby incorporated herein by reference.

Referring first to FIGS. 1 to 3 of the drawings, the catheter or probe 10 described in the above application includes an inner conductor 16 and a coaxial tubular outer conductor 18. The distal or leading end 16a of conductor 16 is connected to the center of a conductive discoid toe plate 22 spaced in front of the outer conductor 18 which space is filled by a discoid dielectric spacer member 24. A hemispherical conductive shell 26 is mounted to the distal face of toe plate 22. Together they form a conductive distal end or tip 10a of probe 10. Shell 26 also defines a fluid-tight space 28 between the shell wall and the toe plate.

The proximal or trailing end of outer conductor 18 is closed by a discoid heel cap 30 connected to conductor 18 and to the proximal end 16b of inner conductor 16 which end extends into an opening 32 at the center of heel cap 30. The proximal end of center conductor 16 is also connected to the distal end of an inner conductor 33 of cable 14. Those two conductors meet in opening 32 with the cable end being anchored to heel cap 30.

The segment of inner conductor 16 within the outer conductor 18 carries a dielectric sleeve 34 and is supported within conductor 18 by a conductive insert or carrier 36 which fits in, and extends the length of, conductor 18, thus forming a coaxial transmission line. The conductor 16 and its sleeve 34 extend along an axial passage 38 in the insert. Insert 36 is in electrical contact with both outer conductor 18 and heel cap 30.

Still referring to FIGS. 1 and 2, a sheath 52 of a dielectric material surrounds the outer conductor 18 of catheter 10. However, that sheath does not extend all the way to the distal end of the conductor, but rather terminates at a selected distance therefrom. The proximal end of sheath 52 blends into cable 14.

A filter circuit 54 and a microwave radiometer circuit 56, arranged in one or more monolithic microwave integrated circuit chips (MMICs), are mounted to the top of insert 36. Also, mounted directly to the inner conductor 16 just ahead of insert 36 is a coupling capacitor 58 which is recessed into the spacer member 24. One terminal of capacitor 58 is connected electrically to conductor 16 and the other is connected by way of a lead (strip or wire) 60 to the first circuit 54 which is, in turn, connected to circuit 56. The output signal from the last circuit 56 as well as certain bias and control voltages are carried on a conductor group 64 which extends along the top of insert or carrier 36 and exits the catheter through a hole 66 in heel cap 30. There, those conductors join corresponding conductors 68 (FIG. 2) which extend along cable 14 to an external control unit (not shown). Also, a ground return conductor 69 from circuit 56 connects to a corresponding conductor 70 in cable 14.

Preferably the radiometer operates at a frequency in the microwave range. A conventional Dicke-type microwave radiometer is disclosed in my U.S. Pat. No. 4,557,272. Similar radiometer designs on a chip are available from Meridian Medical Systems, LLC, the assignee of this application.

Referring now to FIG. 1, basically the inner conductor 16 in catheter 10 comprises an RF coaxial transmission line terminated by the conductive rounded tip 10a. The transmission line is operated at the output signal frequency of a remote transmitter is (not shown). When the transmitter is operative, the transmission line will radiate energy for heating only from the uninsulated segment of the catheter between the catheter tip 10a and the distal end of the dielectric sheath 52. Thus, that segment constitutes a RF heating or transmitting antenna T whose length is determined by the forward or distal extent of sheath 52 on outer conductor 18. In other words, increasing the length of sheath 52 will reduce the exposed length of conductor 18, i.e. the surface that could contact tissue, and, in turn, will reduce the antenna T length. Since the outer conductor 18 is at the same RF potential as conductor 16, it can provide an RF path between the antenna T and the transmitter.

Referring to FIGS. 1 and 3, the conductive catheter tip 10a also comprises a temperature sensing microwave receiving antenna R which can pick up thermal emissions at depth from tissue adjacent to the catheter 10. The segment of conductor 16 from the tip 10a to its junction with capacitor 58 comprises the microwave receiving path and this path continues along the lead strip 60 to filter circuit 54 and thence to radiometer circuit 56. It should be noted that while conductor 33 is basically an extension of conductor 16, it conducts only the RF signal via outer conductor 18, while conductor 16 conducts both the RF and microwave signals. Thus, the probe's antennas T and R are contained in a common structure and basically constitute a single dual frequency antenna.

To enable catheter 10 to simultaneously heat (transmit) and detect temperature (radiometrically sense), a passive diplexer D is integrated into catheter 10 in order to block the transmitter signals from the microwave receiving path and isolate the microwave signals from the signal path from the transmitter. The diplexer D is formed by the filter circuit 54 coupled with lead 60 and capacitor 58 along with a quarter-wave ($\lambda_R/4$) shorted stub S (FIG. 1) constituted by the segment of catheter 10 extending from the connection of capacitor 58 to conductor 16, to the heel cap 30. This quarter wave stub S should be tuned to the frequency of the radiometer, thus providing a low loss path to circuit 56. The diplexer D also includes a high pass filter in at least one of circuits 54, 56.

The tuned length of the stub S, i.e. the catheter segment between capacitor 58 and heel cap 30, is determined by the dielectric constant of the material in sleeve 34 as well as the radiometer frequency. For example, at a radiometer frequency of 4 GHz, when sleeve 34 is of PTFE (K=2.1), a suitable stub length may be 0.5 inch. On the other hand, when a K=9 material is used, the stub length may be reduced to 0.25 inch. For an intermediate length, e.g. 0.38 inch, a K=3.8 material may be used.

For the minimally invasive catheter of interest here, it is essential that the length of stub S be as short as possible. This, in turn, requires that the sleeve 34 material have an especially high dielectric constant, i.e. K=9 or more. Only hard ceramics such as alumina (K=9.8) meet this criterion.

In practice, we have found that it is quite difficult to reliably manufacture at a reasonable cost a thin-wall, e.g. 0.005 in, dielectric sleeve 34 of alumina ceramic. Such sleeves are quite fragile and difficult to make on a high volume basis. Therefore, it would be desirable to be able to provide a probe of the above type which can be made and marketed on a competitive basis with prior medical probes used for this general purpose.

SUMMARY OF THE INVENTION

Accordingly the present invention aims to provide an improved, minimally invasive antenna catheter or probe for simultaneously controllably heating, and sensing the temperature of, fluid or tissue in a human or animal body.

Another object of the invention is provide an integrated antenna catheter including a built-in diplexer and microwave receiver which, when connected to an external control unit containing a transmitter, can simultaneously heat, and detect the temperature of, fluid or tissue adjacent to the catheter.

A further object of the invention is provide such a probe which is simpler and less expensive to make than prior comparable probes of this general type.

Still another object of the invention is to provide a probe of this type which has accurate and reliable operating parameters.

Another object is to provide such a probe which is very small so that it can be used in many minimally invasive applications.

Other objects will, in part, be obvious and will, in part, appear hereinafter.

The invention accordingly comprises the features of construction, combination of elements and arrangement of parts which will be exemplified in the following detailed description and the scope of the invention will be indicated in the claims.

In general, this medical probe incorporates a single, dual frequency antenna structure which can receive from a transmitter, and radiate, an electromagnetic signal of a first frequency capable of heating tissue, and pick up a microwave signal from that tissue of a second frequency indicative of tissue temperature at depth, which received signal may be routed to a receiver contained right in the probe. The antenna has a single center conductor and the two signals are isolated by a diplexer also integrated into the is probe which includes a shorted quarter wave stub in the signal transmitting path and a filter circuit in the signal receiving path.

However, instead of utilizing the center conductor in a coaxial transmission line to form the stub as described in my above application, the stub in the present probe comprises a transmission line of the slab-line or suspended substrate type. This type of transmission line does not require a dielectric sleeve around the center conductor as described in the above prior application. Accordingly, this quarter wave stub is easier and less expensive to make than the prior stub. Consequently, its incorporation into the present probe minimizes the overall cost of same.

Also, as we shall see, the utilization of a slab-line or suspended substrate-type quarter wave stub in the present probe facilitates tuning the impedance of the stub. It also enables the use in the probe of a relatively large diameter center conductor without materially increasing the overall diameter of the probe. This, in turn, enables the center conductor to be formed as a tube by which a cooling or irrigation fluid may be conducted to, and dispensed from, the probe tip.

BRIEF DESCRIPTION OF THE DRAWINGS

For a fuller understanding of the nature and objects of the invention, reference should be made to the following detailed description taken in connection with the accompanying drawings, in which.

DESCRIPTION OF A PREFERRED EMBODIMENT

Figure 4:
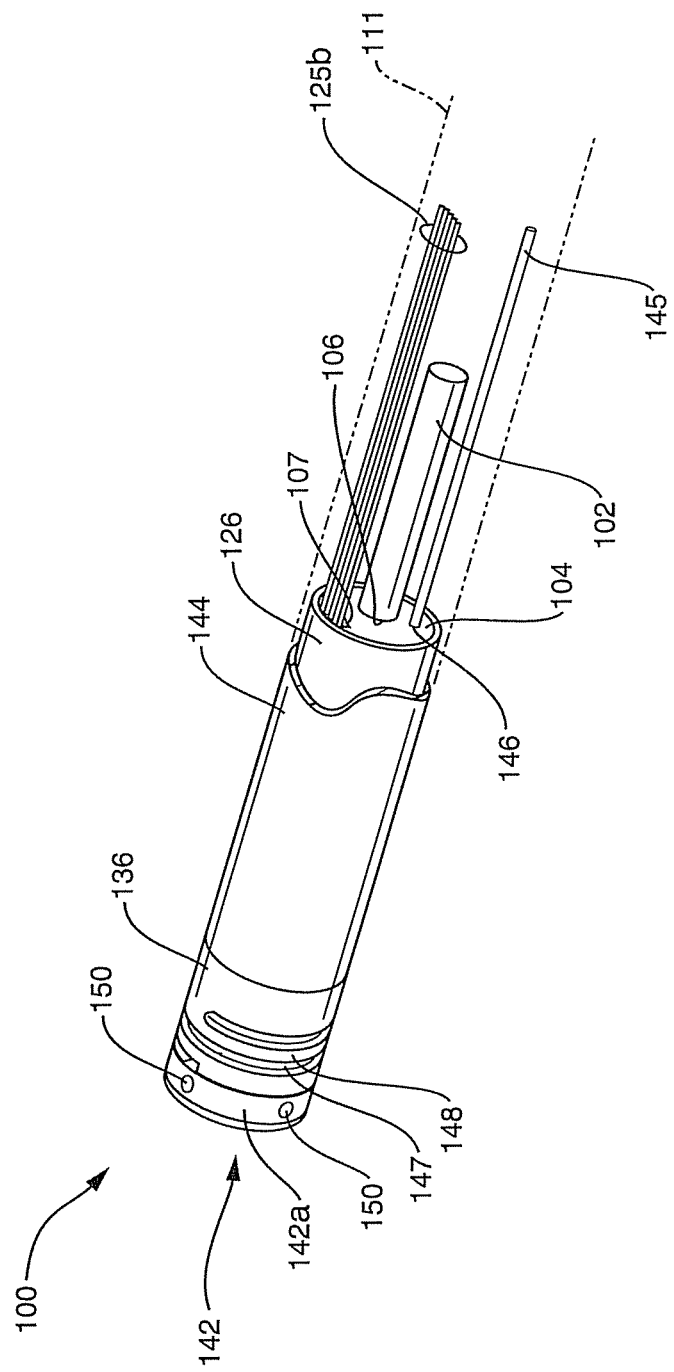
FIG. 4 is a perspective view of a probe incorporating the present invention.
Figure 5:
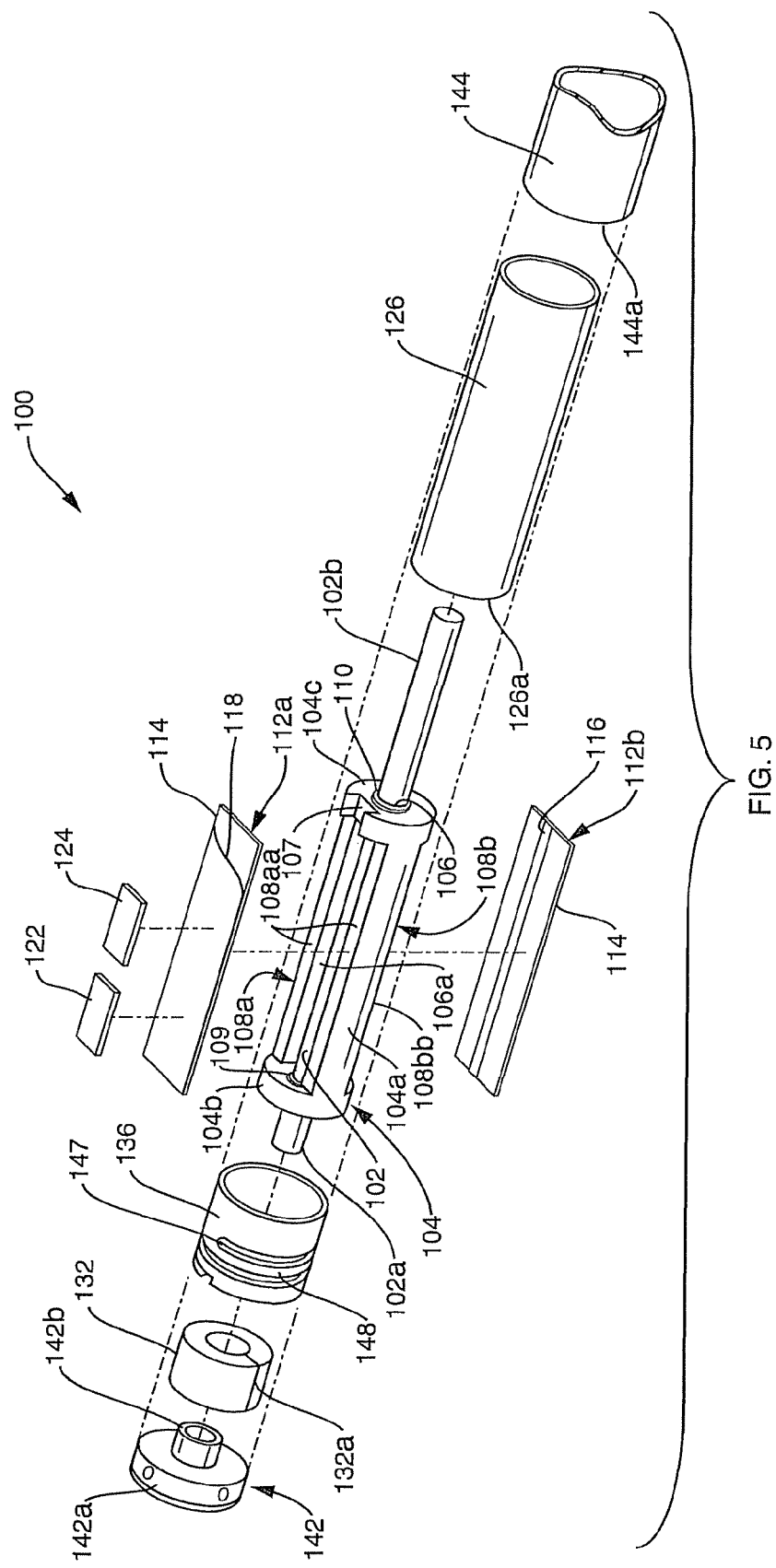
FIG. 5 is an exploded perspective view showing the components of the FIG. 4 probe in greater detail.

Refer now to FIGS. 4 and 5 of the drawings which show the probe of this invention indicated generally at 100. The former figure illustrates the probe fully assembled, while in the latter figure, the probe is in a disassembled state. As seen there, the probe comprises an inner or center conductor 102 supported by a conductive carrier or is insert 104. Carrier 104 is formed from a cylindrical metal body having an axial passage 106 that receives conductor 102. Upper and lower sectors of that body inboard the ends thereof are milled away to expose passage 106 and conductor 102 therein and to form upper and lower substantially parallel flats 108a and 108b. Flat 108a is composed of coplanar rectangular areas 108aa spaced on opposite sides of conductor 102 near the top thereof. Likewise, flat 108b comprises two coplanar rectangular areas 108bb spaced on opposite sides of conductor 102 near the bottom thereof. Thus, carrier 104 is composed of a center segment 104a containing the flats and distal and proximal end segments 104b and 104c, respectively, which remain cylindrical, except that a vertical groove 107 is formed in proximal segment 104c for reasons to be described later.

The center conductor 102 is fixed coaxially within passage 106 by means of an electrically insulating collar or bushing 109, e.g. of PTFE, press fit into the passage 106 at the distal end segment 104b of the carrier and by a weld 110 to the passage wall or by an electrically conductive collar or bushing (not shown) at the carrier proximal segment 104c. Thus, there is a short circuit between conductor 102 and carrier 104 at the proximal end of the carrier, while an open circuit is present therebetween at the distal end of the carrier. In the carrier center segment 104a, the walls 106a (FIG. 8) of passage 106 are spaced from center conductor 102. This forms a quarter wave stub S (FIG. 7) in the probe that will be described in detail later. Conductor 102 has a distal end segment 102a which extends beyond the distal end of carrier 104 a selected distance to be described is later and a proximal end segment 102*b* which extends from the proximal end of probe 100 and connects to the center conductor of a coaxial cable 111 similar to cable 14 in FIG. 1.

Figure 6:
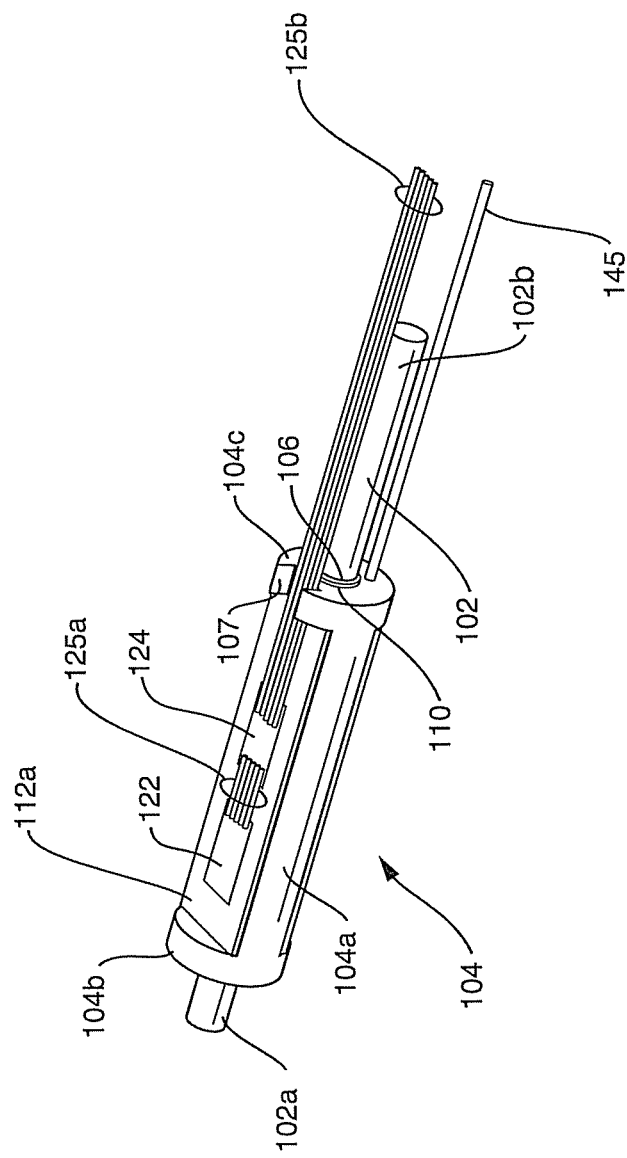
FIG. 6 is a similar view showing certain assembled elements of the probe.
Figure 7:
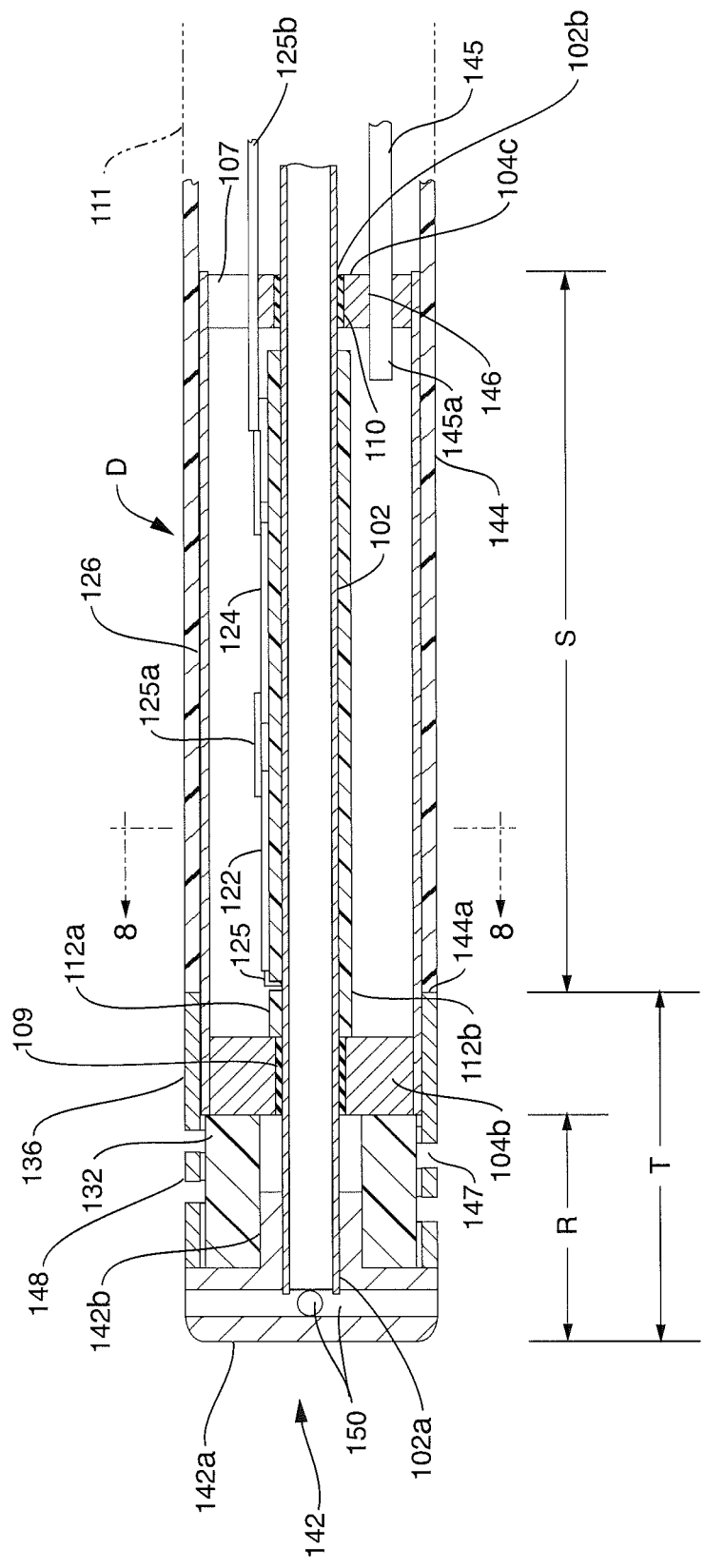
FIG. 7 is a view in axial section on a larger scale of the fully assembled probe.
Figure 8:
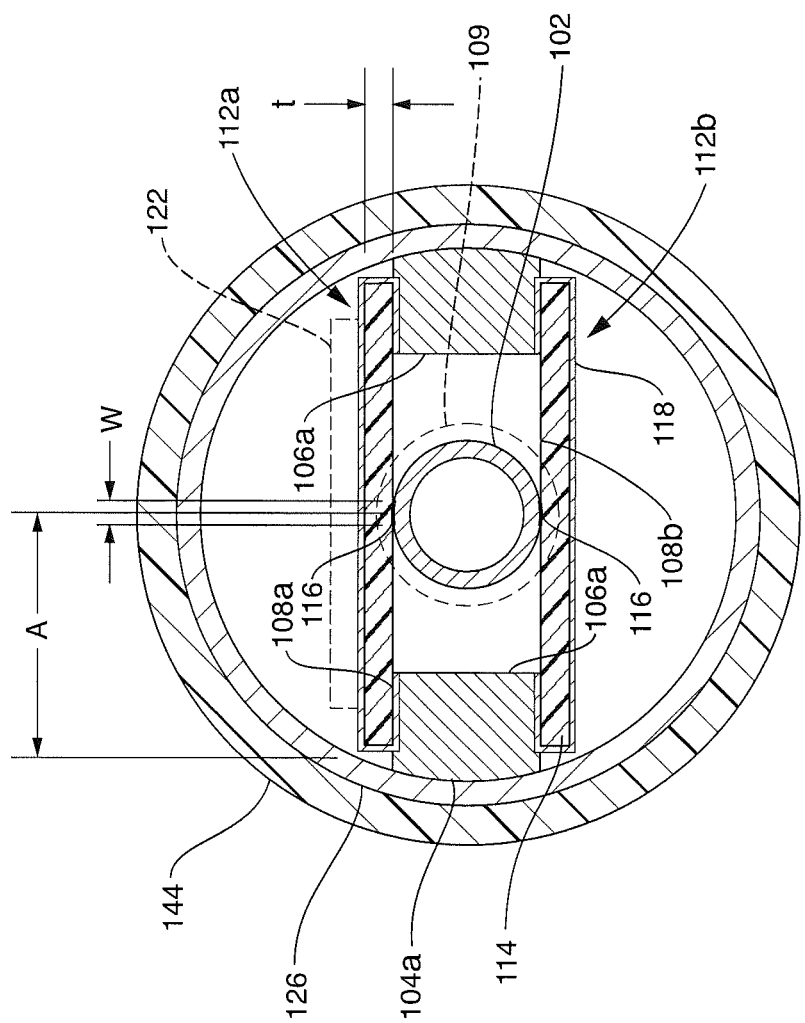
FIG. 8 is a sectional view on a still larger scale taken along line 8-8 of FIG. 7

As shown in FIGS. 5-8, mounted to the upper and lower flats 108*a* and 108*b* of carrier 104 is a pair of opposed, parallel, mirror-image, generally rectangular plates 112*a* and 112*b*. Each plate 112*a*, 112*b* comprises a thin, e.g. 0.005 in., substrate 114 formed of an electrically insulating material having a high dielectric constant. Printed, plated or otherwise formed on the opposing or facing surfaces of substrates 114 are axially centered, lengthwise conductive strips 116, preferably 0.013-0.016 mm wide, which extend the entire lengths of substrates 114. Also, the opposite or away-facing surfaces of substrates 114 are plated with conductive layers 118, e.g. of gold. As best seen in FIG. 8, the side edges of layers 118 wrap around the side edges of the substrates.

When the probe is being assembled, the plate 112*a* is seated on the upper flat 108*a* of carrier 104 and the lower plate 112*b* is likewise seated on the lower flat 108*b* as shown in FIGS. 7 and 8 so that the center conductor 102 is contacted from above and below by the conductive strips 116 of the upper and lower plates and the layer 118 side edges of those plates contact carrier segment 104*a*. A suitable conductive epoxy or cement should be applied between those contacting surfaces to secure the plates in place.

As shown in FIGS. 6-8, at least one of the plates, e.g. plate 112*a*, functions also as a support surface for one or more monolithic integrated circuit chips (MMICs), e.g. chips 122 and 124. The chip(s) may include a coupling capacitor connected by a lead 125 (FIG. 7) to center conductor 102 and the usual components of a radiometer such as a Dicke switch, a noise source to provide a reference temperature, amplifier stages, a band pass filter to establish the radiometer bandwidth, additional gain stages if needed, a detector and buffer amplifier. Due to the very small profile of the present probe 100, the above circuit components are actually organized in a string of four chips. In any event, the chip(s) may be secured to the metal layer 118 of plate 112*a* by a suitable conductive adhesive so that that layer which, as described above, is grounded to the insert 104 may function as a ground plane for those chips. The plates also conduct heat away from the chips to conductor 102 and carrier 104. As best seen in FIG. 6, various leads 125*a* connect the chips to each other and other leads 125*b* extend through carrier slot 107 and connect the last chip 124 in the string, i.e. the radiometer output, to corresponding conductors of the cable 111 leading to a remote unit similar to the one described in the above application. In the illustrated probe, the output of the radiometer is actually a video output adapted to be coupled to a remote interface box.

As shown in FIGS. 5, 7 and 8, a tubular outer conductor 126 may be slid onto carrier 104 from an end thereof so that it snugly engages around the carrier with its proximal and distal ends coinciding with the corresponding ends of the carrier as best seen in FIG. 7. The conductor 126 may be fixed in place by a conductive epoxy or cement applied around the carrier segments 104*b* and 104*c*.

Probe 100 also includes an annular dielectric spacer 132, e.g. of PTFE, which is centered on the distal end of carrier 104 and surrounds the conductor segment 102*a*. The spacer may have a slit 132*a* enabling it to be engaged around that conductor segment from the side thereof. As shown in FIG. 7, the spacer 132 may be held in place is by a conductive collar 136 which encircles the spacer and is long enough to slidably engage over a distal end segment of outer conductor 126. The collar may be press fit around that conductor and carrier segment 104*b* to hold it in place and to electrically connect all those elements.

As shown in FIGS. 4, 5 and 7, the distal end of the probe 100 is closed off by a conductive tip 142 which, in axial section, is T shaped. That is, the tip 142 has a discoid head 142*a* which constitutes the distal end of the probe and an axially extending tubular neck 142*b*. The conductor segment 102*a* is long enough to extend beyond the distal end of the spacer 132 into the axial passage in neck 104*b*. The tip may be secured in place by conductive adhesive applied around the distal end of conductor segment 102*a* and at the distal end or edge of collar 136. When the tip is in place, the conductor segment 102*a* and tip 104 form a receiving antenna R (FIG. 7) similar to the one described in connection with FIG. 1.

The final component of probe 100 is a dielectric sheath 144 which may be engaged over the rear end of outer conductor 126 and slid forwardly until its distal end 144*a* is spaced a selected distance behind the distal end of tip 142. The conductors 102 and 126 of probe 100 comprise a RF transmission line terminated by the tip 104. When the probe is operative, the transmission line radiates energy for heating tissue only from the uninsulated segment of the probe between tip 104 and the distal end 144*a* of the sheath 144. That segment thus constitutes a heating or transmitting antenna T (FIG. 7), the antennas R and T forming a single dual frequency antenna structure.

The proximal ends of the center conductor segment 102*b*, outer conductor 126 and sheath 144 may be connected, respectively, to the inner and outer conductors and outer sheath of cable 111 that leads to an external control unit as described in the above application. Alternatively, those elements may be extensions of the corresponding components of cable 111. In any event, that cable 111 connects the center conductor 102 to the output of a transmitter which transmits a RF heating signal at a selected heating frequency, e.g. 500 GHz, to antenna T.

As shown in FIGS. 4 and 7, if desired, that cable 111 may include a probe steering wire 145 whose leading end 145*a* may be secured to the wall of a passage 146 in carrier segment 104*c*.

Preferably, a helical through slot 147 is provided in collar 136 as shown in FIGS. 4, 5 and 7. The collar material left between the slot turns essentially forms a helical wire 148 that bridges the spacer 132. Wire 148 is found to improve the RF heating pattern of transmitting antenna T without materially degrading the microwave antenna pattern of receiving antenna R.

The inner or center conductor 102 may be a solid wire as shown in FIG. 6. More preferably, it is formed as a tube as seen in FIGS. 7 and 8. This enables the conductor 102 to carry an irrigation fluid or coolant to the interior of probe tip 142 for distribution therefrom through radial passages 150 in tip head 142*a* that communicate with the distal end of the axial passage in tip neck 142*b*.

As shown in FIG. 8, when the plates 112*a* and 112*b* are seated on and secured to the upper and lower flats 108*a* and 108*b*, respectively, of carrier 104, the conductive strips 116, 116 of those members are electrically connected to the center conductor 102 at the top and bottom thereof so that conductor 102 constitutes the center conductor of a slab line-type transmission line whose ground plane is comprised of layers 118, 118.

When the probe is operative, a microwave field exists within the substrate 114 and is concentrated between the center conductor 102 and layers 118, 118. Preferably, as noted here, conductive epoxy is applied between conductor 102 and strips 116 to ensure that no air gaps exist there because such a gap would have a significant effect on the impedance of the transmission line as the highest field parts are closest to conductor 102.

In any event, plates 112a, 112b and the conductor 102 segment together with carrier 104 form a quarter wave $$\left(\frac{\lambda_R}{4}\right)$$

stub S which should be tuned to the frequency of the radiometer circuit 124, e.g. 4 GHz. Clearly it much easier to manufacture the thin, flat plated substrates 114 of a high dielectric material such as alumina ceramic (K=9.8) than it is to surround conductor 102 with a thin-walled ceramic sleeve, such as sleeve 34 in FIG. 1, to create the stub S.

Figure 1:
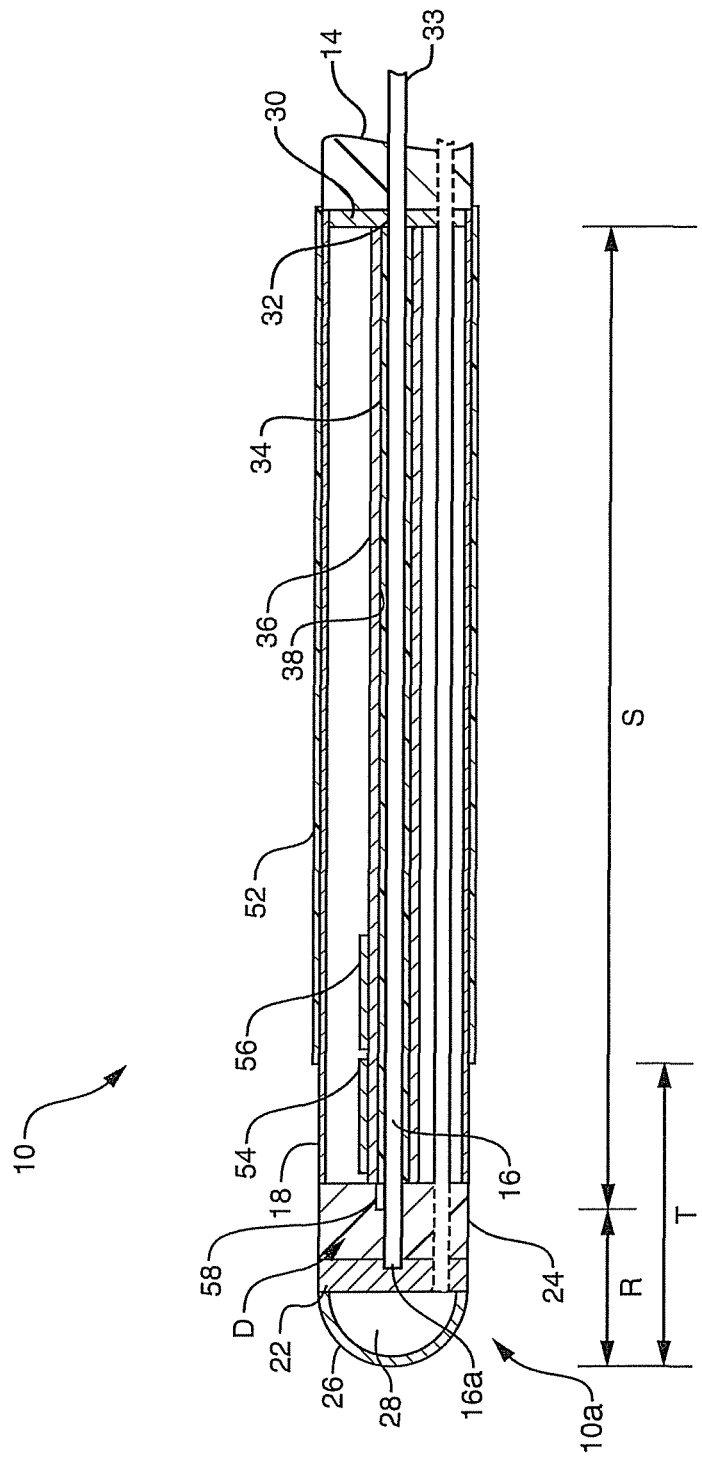
FIG. 1, already described, is a longitudinal sectional view of the probe described in the above pending application.
Figure 2:
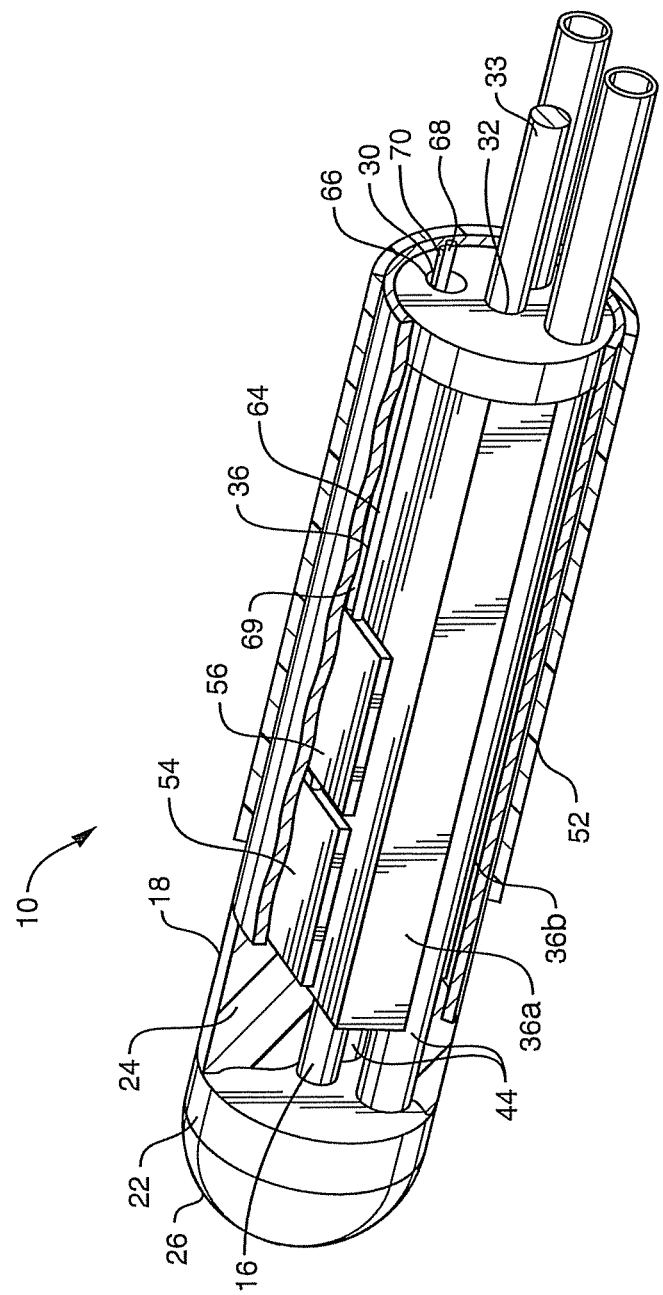
FIG. 2, already described, is a fragmentary perspective view with parts broken away thereof.
Figure 3:
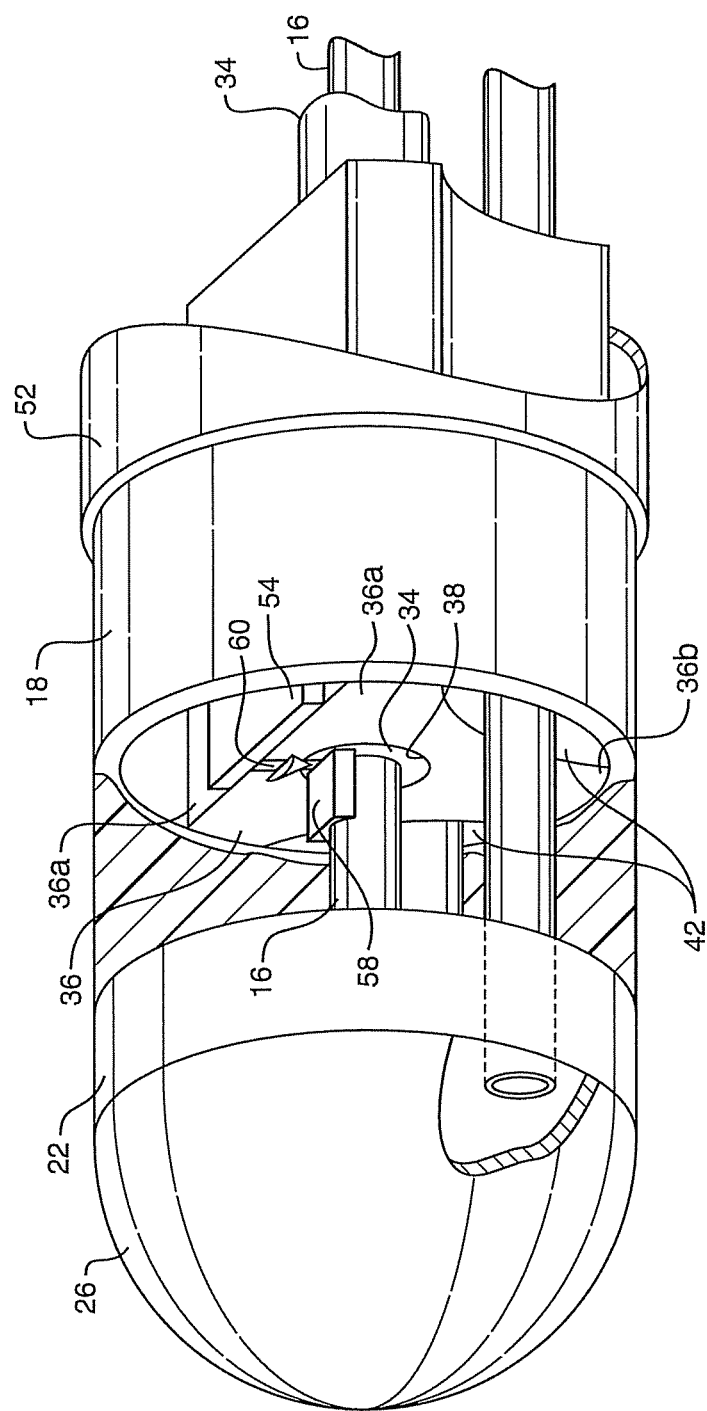
FIG. 3, already described, is a similar view on a larger scale showing a portion of the FIG. 1 probe in greater detail.

As described in connection with the FIG. 1 probe, the quarter wave stub S, tuned to the center frequency of the radiometer circuit 124 along with components in the chips 122, 124 form a low pass filter in the signal transmitting path to the antenna T, while other components of the chips comprise a high pass or band pass filter in the signal receiving path from the antenna to the radiometer. The combination constitutes a passive diplexer D which prevents the lower frequency transmitter signals on the signal transmitting path from antenna T from reaching the radiometer, while isolating the path to the transmitter from the higher frequency signals on the signal receiving path from the antenna.

Referring to FIGS. 7 and 8, the impedance of the quarter wave stub S depends upon the K value and thickness t of the substrates 114 of the two plates 112a, 112b and the spacing of the center conductor 102 from the walls 106a, 106a of passage 106 in the carrier center segment 104a. Since the center conductor 102 is not surrounded by a ceramic sleeve, those walls can be moved closer to the center conductor, enabling accurate tuning of the suspended substrate transmission line impedance while minimizing the overall diameter of the probe 100. As noted above, the length of the stub S is also minimized by making substrate 114 of a dielectric material which has an especially high K value.

In one working embodiment of the probe 100, which is only about 0.43 in. long and about 0.08 in. in diameter, the components of the probe have the following dimensions:

| Part | Dimension (in.) |
|---|---|
| Conductor 102 | 0.020 OD; 0.016 ID (if present) |
| Substrate 114 (K = 9.8) | 0.065 wide; t = 0.005 |
| Strips 116 | W = 0.015 |
| Air gap between 102 and each 106a | 0.015 |

Despite the fact that all the components of the probe's diplexer and radiometer can be mounted within the confines of the probe, the overall length and diameter of the probe 100 can still be kept to a minimum which is an important requirement for probes used in minimally invasive applications.

Figure 9:
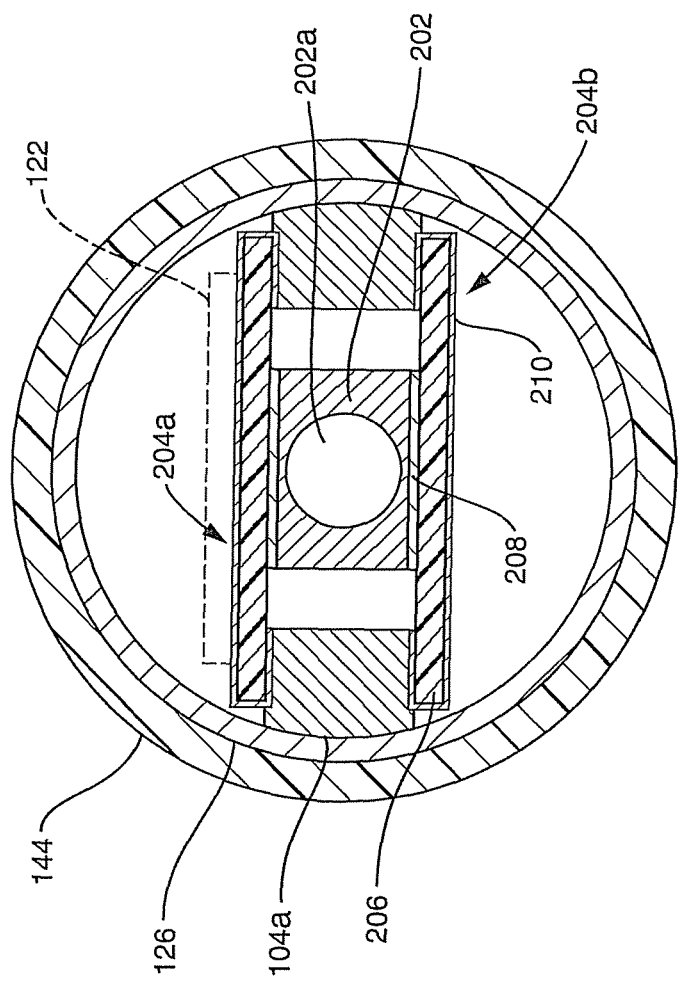
FIG. 9 is a sectional view similar to FIG. 8 illustrating a second probe embodiment incorporating the invention.

Referring now to FIG. 9 of the drawings, instead of the center conductor 102 (FIG. 8) having a circular cross section, it may have a noncircular, e.g. rectangular, cross section as shown at 202 in FIG. 9. This broadens the contact surface between that conductor and plates 204a and 204b mounted to carrier segment 104a above and below conductor 202. As before, each plate comprises a dielectric substrate 206, a conductive layer 208 grounded to carrier segment 104a and a broad conductive strip 210 facing the center conductor 202. In this case, each strip, instead of being printed on the substrate, is a conductive epoxy film applied to the substrate.

Thus, in this embodiment, the forces exerted by conductor 206 on the ceramic substrate are distributed over a relatively large area so as to minimize the chances of cracking the thin ceramic substrates 206 of plate 204a, 204b. Also, such large-area contact between the plates and conductor 202 widens the thermal path from the chip(s) 122, 124 to conductor 202 and any fluid therein, thus optimizing the cooling of the chip(s). In addition, the thickness of the epoxy strips 208 may be carefully controlled to adjust the impedance of the transmission line.

Figure 10:
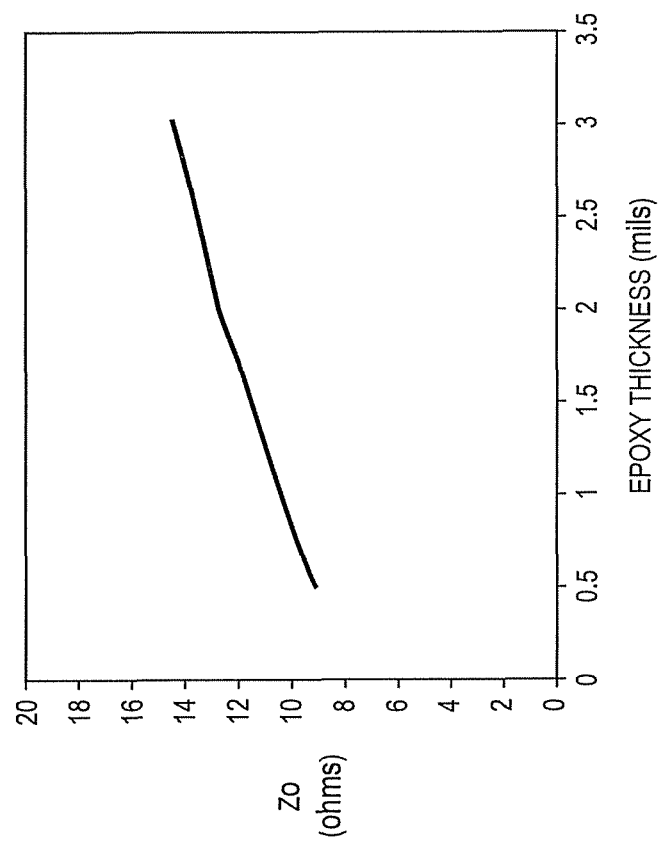
FIG. 10 is a graphical diagram showing certain operating parameters of the FIG. 9 probe embodiment.

FIG. 10 is a graph showing how that impedance varies with the thickness of the epoxy film.

The above described probes can transmit and receive signals simultaneously to both heat tissue or fluid and detect the temperature of that tissue or fluid in real time, thus enabling the efficient performance of various medical procedures. The fact that the diplexer D and radiometer circuit 124 may be incorporated right into the probes 100 and 200 enables the probes to provide very precise and noise-free temperature measurements in a minimum amount of time.

It will thus be seen that the objects set forth above, among those made apparent from the preceding description, are efficiently attained and since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

The invention claimed is:

1. A radiometric heating/sensing probe for radiating electromagnetic waves of a first frequency capable of heating tissue and detecting electromagnetic waves of a second frequency emitted by the tissue indicating tissue temperature, said probe comprising a dual frequency antenna at a distal end of the probe;
   a signal transmitting path to the antenna;
   a signal receiving path from the antenna;
   a diplexer connected inside the probe between said paths, said diplexer including
      a quarter wave stub in the form of a shorted slab line type transmission line in the signal transmitting path that passes first frequency signals and blocks second frequency signals, said transmission line including a center conductor and a pair of substantially parallel ground planes bracketing the center conductor and spaced therefrom by a dielectric material, and
      a filter circuit in the signal receiving path that passes second frequency signals and blocks first frequency signals.

2. The probe defined in claim 1 wherein the filter circuit is a chip mounted on one of the ground planes.

3. The probe defined in claim 1 and further including a solid state radiometer mounted to one of the ground planes.

4. The probe defined in claim 1 wherein the center conductor is tubular.

5. A radiometric heating/sensing probe for radiating electromagnetic waves of a first frequency capable of heating tissue and detecting electromagnetic waves of a second frequency emitted by the tissue indicating tissue temperature, said probe comprising
   a dual frequency antenna at a distal end of the probe;
   a signal transmitting path to the antenna;
   a signal receiving path from the antenna;

a diplexer connected between said paths inside the probe, said diplexer including a quarter wave stub in the form of a shorted slab line type transmission line in the signal transmitting path that passes first frequency signals and blocks second frequency signals, said transmission line including
 a center conductor,
 a pair of substantially parallel ground planes bracketing the center conductor and spaced therefrom by a dielectric material,
 a coaxial conductive carrier spaced radially out from the conductor, the conductor and carrier each having proximal and distal ends, the distal end of the conductor extending beyond the distal end of the carrier and the proximal end of the carrier being shorted to the conductor;
 a pair of opposite flats on the carrier between the ends thereof which exposes the conductor, and
 a pair of substantially parallel plates mounted to the pair of flats, each plate including a substrate of said dielectric material and having opposite faces, a conductive strip on one face of the substrate, said strip extending parallel to and contacting the conductor and a conductive layer on the other face of each substrate in electrical contact with the carrier, each conductive layer constituting a said ground plane, and
a filter circuit in the signal receiving path that passes second frequency signals and blocks first frequency signals.

6. The probe defined in claim 5 wherein at least a segment of the conductor in the carrier has a round cross section.

7. The probe defined in claim 6 wherein at least a segment of the conductor in the carrier has a rectangular cross section.

8. The probe defined in claim 5 wherein said filter circuit is mounted to the conductive layer of one of said plates.

9. The probe defined in claim 8 and further including a radiometer mounted to the conductive layer of one of said plates and being electrically connected to the filter circuit.

10. The probe defined in claim 9 wherein the filter circuit and radiometer comprise one or more monolithic microwave integrated circuit chips.

11. The probe defined in claim 5
 wherein the conductor comprises a hollow tube, and
 further including one or more passages at the distal end of said tube by which a fluid may be dispensed from said probe.

12. The probe defined in claim 5 wherein said antenna comprises
 said distal end of said center conductor;
 an outer conductor surrounding the carrier and the distal end of the center conductor, and
 a dielectric sheath surrounding the carrier but not the distal end of the center conductor.

13. The probe defined in claim 5 wherein the center conductor is tubular.

14. A radiometric heating/sensing probe for radiating electromagnetic waves of a first frequency capable of heating tissue and detecting electromagnetic waves of a second frequency emitted by the tissue indicative of tissue temperature, said probe comprising
 an electrically conductive carrier having proximal and distal ends and an axial passage extending between said ends;
 an inner conductor received in said passage, said inner conductor being shorted to the proximal end of the carrier and having a distal end extending beyond the distal end of the carrier;
 an outer conductor surrounding the carrier and in electrical contact therewith, said inner and outer conductors forming a dual frequency antenna at a distal end of the probe;
 a signal transmitting path to the antenna;
 a signal receiving path from the antenna;
 a quarter wave stub at said second frequency in the signal transmitting path, said stub including
 said inner conductor and carrier;
 a pair of diametrically opposite flats on the carrier between the ends thereof which exposes the inner conductor, and
 a pair of plates mounted to the pair of flats, each plate including a dielectric substrate having opposite faces, a conductive strip on one face of the substrate extending parallel to and in electrical contact with the inner conductor and a conductive layer on the opposite face in electrical contact with the carrier, said stub forming a filter that passes first frequency signals and blocks second frequency signals.

15. The probe defined in claim 14 and further including a filter circuit that passes second frequency signals and blocks first frequency signals mounted to the conductive layer of one of said plates and being electrically coupled to the inner conductor between the antenna and the stub, said stub and filter circuit together constituting a diplexer inside the probe.

16. The probe defined in the claim 15 and further including a microwave receiver mounted to the conductive layer of one of said plates and being electrically connected to the filter circuit.

17. The probe defined in claim 16 wherein the filter circuit and receiver comprise one or more monolithic microwave integrated circuits.

18. The probe defined in claim 14 wherein at least a segment of the inner conductor in the carrier has a round cross section.

19. The probe defined in claim 14 wherein at least a segment of the inner conductor in the carrier has a rectangular cross section.

20. The probe defined in claim 14 wherein the inner conductor is tubular.

* * * * *

UNITED STATES PATENT AND TRADEMARK OFFICE
CERTIFICATE OF CORRECTION

PATENT NO. : 8,515,554 B2
APPLICATION NO. : 12/626004
DATED : August 20, 2013
INVENTOR(S) : Kenneth L. Carr It is certified that error appears in the above-identified patent and that said Letters Patent is hereby corrected as shown below:

In the Specifications

In col. 2, line 15:
transmitter is (not shown). When the transmitter is operative, In col. 3, line 47:
by a diplexer also integrated into the is probe which includes In col. 4, line 38:
by a conductive carrier or is insert 104. Carrier 104 is formed In col. 4, line 67:
distance to be described is later and a proximal end segment In col. 5, line 62:
spacer 132 may be held in place is by a conductive collar 136

Signed and Sealed this
Tenth Day of December, 2013

Margaret A. Focarino
*Commissioner for Patents of the United States Patent and Trademark Office*